United States Patent [19]

Benson et al.

[11] 4,088,760
[45] May 9, 1978

[54] TESTOSTERONE 5α-REDUCTASE INHIBITORS

[75] Inventors: Harvey D. Benson; Thomas R. Blohm, both of Cincinnati, Ohio

[73] Assignee: Richardson-Merrell Inc., Wilton, Conn.

[21] Appl. No.: 698,824

[22] Filed: Jun. 23, 1976

[51] Int. Cl.² ........................ C07J 9/00; A61K 31/56
[52] U.S. Cl. .................................. 424/242; 260/397.1; 260/397.2; 260/397.4; 260/239.55 C
[58] Field of Search ..................... 260/397.1; 424/242, 424/238

[56] References Cited

U.S. PATENT DOCUMENTS

| | | | |
|---|---|---|---|
| 3,153,615 | 10/1964 | Bosshardt et al. | 424/238 |
| 3,535,312 | 10/1970 | Philippson et al. | 260/239.5 |
| 3,560,558 | 2/1971 | Hayakawa et al. | 260/397.1 |
| 3,917,829 | 11/1975 | Voight et al. | 424/242 |

FOREIGN PATENT DOCUMENTS 1,118,976  7/1968  United Kingdom ............... 260/239.5

OTHER PUBLICATIONS

Chemical Abstracts, vol. 70, (1969), Pars. 88,067(f).
Chemical Abstracts, vol. 74, (1971), Pars. 29,155(t).

*Primary Examiner*—Elbert L. Roberts
*Attorney, Agent, or Firm*—L. Ruth Hattan; Eugene O. Retter; George W. Rauchfuss, Jr.

[57] ABSTRACT

Compounds of the following general formula are testosterone 5α-reductase inhibitors rendering said compounds useful in the treatment of acne and oily skin:

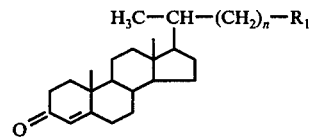

wherein $n$ is an integer of from 0 to 4; $R_1$ is —COOR$_2$, —CONR$_3$R$_4$, —CHO or —CH$_2$OR$_5$; $R_2$ is hydrogen, a straight or branched lower alkyl group of from 1 to 4 carbon atoms, or benzyl; each of $R_3$ and $R_4$ is hydrogen or a straight or branched lower alkyl group of from 1 to 4 carbon atoms; and $R_5$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched, or cycloalkylcarbonyl wherein the cycloalkyl moiety has from 5 to 10 carbon atoms.

12 Claims, No Drawings

TESTOSTERONE 5α-REDUCTASE INHIBITORS

FIELD OF INVENTION

This invention relates to methods of using steroidal compounds as inhibitors of testosterone 5α-reductase in the treatment of acne and oily skin.

DESCRIPTION OF THE PRIOR ART

It is known that skin responds to androgens and is an active site of androgen metabolism. The androgen testosterone is metabolized in the skin to dihydrotestosterone (DHT) which is a more potent androgen than testosterone. As set out in Arch. Dermatol. 111, 1496 (1975) there is considerable evidence that DHT is involved in the pathogenesis of acne as well as other androgen associated conditions. Studies in the hamster flank organ, which is an androgen dependent sebaceous structure, indicate that DHT stimulates the growth of this structure. It has been found that acne-bearing skin produces from 2 to 20 times more DHT than normal skin. Therefore, it is believed that agents capable of blocking the formation of DHT would be effective in the treatment of an acne condition. Testosterone is converted to DHT by the enzymatic action of testosterone 5α-reductase. One possible means of blocking the formation of DHT is to inhibit the activity of testosterone 5α-reductase. More desirably, the activity of the 5α-reductase enzymes is inhibited locally, that is, in the region of the acne-bearing skin without exerting a systemic effect.

Several agents, for example, progesterone, androst-4-ene-3,17-dione, deoxycorticosterone and androst-4-ene-3-keto-17β-carboxylic acid, are known to be effective inhibitors of testosterone 5α-reductase in human skin. Structural requirements for effective testosterone 5α-reductase inhibitors have been defined to include the $\Delta^4$-3-keto configuration in the A-steroid ring with a substituent at the 17β-position of the D-ring. W. Voigt and F. L. Hsia in J. Biol. Chem. 248, 4280 (1973) and U.S. Pat. No. 3,917,829, issued Nov. 4, 1975, have further characterized the substituent required at the 17β-position as one possessing an electronegative group, particularly a substituent having either an oxygen atom bonded to a carboxy carbon or having an oxygen attached to the $C_{20}$ carbon atom. Voigt and Hsia have indicated that based on their findings the size of the 17β-substituent is not too critical, but there is criticality in the location of the oxygen function contained in the substituent, one or more such functions being desired at or near the 17- position carbon atom and have indicated that this area of the D-ring being rendered electronegative by the substituent binds with a hydrophilic region of the 5α-reductase enzyme. In further defining the required 17β-oxy groups or substituents containing an oxygen function, Voigt and Hsia describe the following substituents:

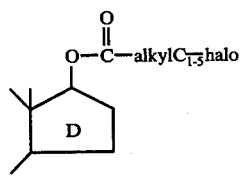

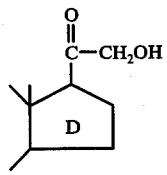

-continued

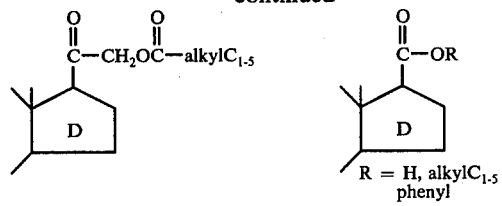

In each type of substituent described by Voigt and Hsia the 17-position carbon atom is either bonded directly to an oxygen atom or to a carbonyl group in the β-configuration, the carboxylic acid group being preferred, creating a relatively high degree of electronegativity at the 17β-position.

Therefore, in light of the teachings of Voigt and Hsia it is surprising to discover that the compounds employed in the present invention are effective inhibitors of testosterone 5α-reductase inasmuch as the substituent at the 17β-position of said compounds does not have an oxygen function or a carbonyl group attached thereto. It is even more surprising to find that the preferred 17β-COOH derivative of Voigt and Hsia is less effective than the closest analog employed in the present invention, that is, α-methyl-17β-acetic acid

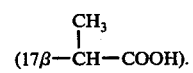

The compounds employed in the present invention offer another advantage in that they can be obtained economically.

SUMMARY OF THE INVENTION

Compounds of the following general Formula I are inhibitors of testosterone 5α-reductase rendering said compounds useful in the treatment of acne or an oily skin condition.

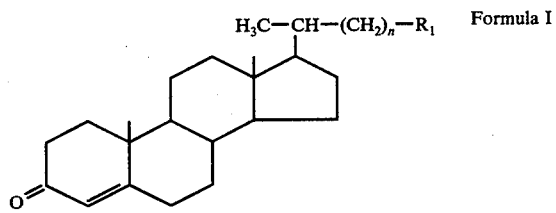

In the above general Formula I n is an integer of from 0 to 4; $R_1$ is —$COOR_2$, —$CONR_3R_4$, —CHO or —$CH_2OR_5$; $R_2$ is hydrogen, a straight or branched lower alkyl group of from 1 to 4 carbon atoms, or benzyl; each of $R_3$ and $R_4$ is hydrogen or a straight or branched lower alkyl group from from 1 to 4 carbon atoms; and $R_5$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched, or cycloalkylcarbonyl wherein the cycloalkyl moiety has from 5 to 10 carbon atoms.

Illustrative examples of straight or branched lower alkyl groups containing from 1 to 4 carbon atoms as used in defining the compounds of general Formula I are methyl, ethyl, n-propyl, isopropyl, n-butyl, sec-butyl, isobutyl and tert-butyl.

The term alkylcarbonyl as used in defining the compounds employed in the present invention is taken to mean a group of the structure

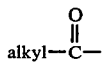

wherein the alkyl moiety has from 1 to 20 carbon atoms and can be a straight chain or a branched chain. Illustrative examples of the alkyl moiety in the substituent alkylcarbonyl group are methyl, ethyl, n-propyl, isopropyl, n-butyl, sec-butyl, tert-butyl, n-pentyl, neopentyl, pivalyl, hexyl, heptyl, octyl, 2,4-dimethyloctyl, undecyl, 9-methylundecyl, pentadecyl, hexadecyl, dodecyl, 2,4,6-trimethyldecyl, heptadecyl, decyl, octadecyl, nonadecyl and didecyl.

The term phenylalkylcarbonyl as used in defining the compounds employed in the present invention is taken to mean a substituent group of the structure

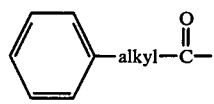

wherein the alkyl moiety, which may also be referred to as an alkylene moiety, has from 1 to 6 carbon atoms and can be a straight chain or a branched chain. Illustrative examples of the alkyl moiety in the substituent phenylalkylcarbonyl group are methyl, ethyl, n-propyl, n-butyl, n-pentyl, hexyl, isopropyl, sec-butyl, tert-butyl, and neopentyl.

Illustrative examples of cycloalkylcarbonyl groups which may be present in the compounds employed in the present invention as the substituent $R_5$ in general Formula I are cyclopentanecarbonyl, cyclohexanecarbonyl, cyclooctanecarbonyl, 1- or 2-norbornanecarbonyl and 1- or 2-adamantanecarbonyl.

It is apparent from the foregoing general Formula I that the compounds employed in the present invention are $\Delta^4$-3-keto steroid derivatives substituted at the 17$\beta$-position with a carboxylic acid containing substituent, as represented by the following general Formula II, or an ester or amide thereof, as represented respectively by the following general Formulas III and IV, or a carboxaldehyde containing substituent, as represented by the following general Formula V, or a methanol containing substituent or ester thereof, as represented respectively by the following general Formulas VI and VII:

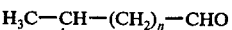
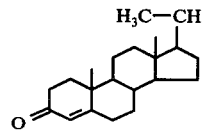  Formula II

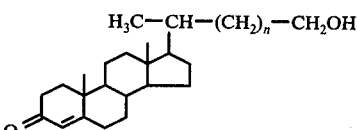  Formula III

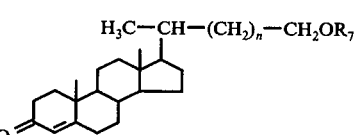  Formula IV

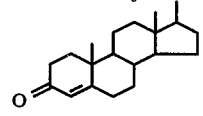  Formula V

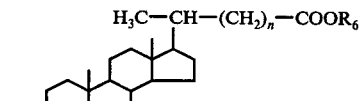  Formula VI

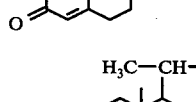
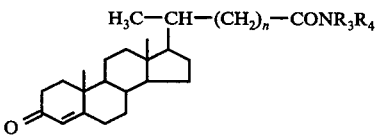  Formula VII
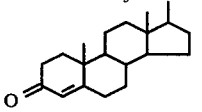

In the above general Formulas II to VII $n$ is an integer of from 0 to 4. In general Formula III, $R_6$ is a straight or branched lower alkyl group having from 1 to 4 carbon atoms as defined hereinabove or benzyl. In general Formula IV each of $R_3$ and $R_4$ is hydrogen or a straight or branched lower alkyl group having from 1 to 4 carbon atoms as defined hereinabove. In general Formula VII, $R_7$ is alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched, or cycloalkylcarbonyl wherein the cycloalkyl moiety has from 5 to 10 carbon atoms as defined hereinabove.

The use as inhibitors of testosterone 5$\alpha$-reductase and in the treatment of acne and oily skin of the compounds of general Formulas II and III wherein $n$ is the integer 0 representing a more preferred embodiment. As to the compounds of general Formula III, the methyl ester derivatives are particularly preferred. The use of the compounds of general Formulas V and VI represent other preferred embodiments of this invention with the use of those compounds wherein $n$ is the integer 0 representing a more preferred embodiment.

The nomenclature of the compounds of general Formulas I to VII varies with the definition of the integer as represented by $n$. Compounds employed herein wherein n is 0 or 1 are named as pregnane derivatives. Compounds wherein $n$ is 2 are named as cholane derivatives. Compounds wherein $n$ is 3, and R is —COOR$_2$, —CONR$_3$R$_4$ or —CHO are named as cholane derivatives. Compounds wherein $n$ is 3, and R is —CH$_2$OR$_5$ are named as cholestane derivatives. Compounds wherein $n$ is 4 are named as cholestane derivatives. The following tabulation illustrates the naming of representative compounds of general Formulas I to VII.

TABLE I

| n | R | Compound Name |
|---|---|---|
| 0 | —COOH | 3-Oxopregn-4-ene-20-carboxylic acid |
| 0 | *—COOCH$_3$ | Methyl 3-oxopregn-4-ene-20-carboxylate |
| 0 | *—COObenzyl | Benzyl 3-oxopregn-4-ene-20-carboxylate |
| 0 | **—CONNH$_2$ | 3-Oxopregn-4-ene-20-carboxamide |
| 0 | **—CON(CH$_3$)$_2$ | N,N-Dimethyl-3-oxopregn-4-ene-20-carboxamide |
| 0 | —CHO | 3-Oxopregn-4-ene-20-carboxaldehyde |
| 0 | —CH$_2$OH | 21-Hydroxy-20-methyl- |

TABLE I-continued

| n | R | Compound Name |
|---|---|---|
| 0 | #—CH$_2$OCCH$_2$CH$_3$ (O double bond) | pregn-4-en-3-one 21-(1-Oxopropoxy)-20-methylpregn-4-en-3-one |
| 1 | —COOH | 20-Methyl-3-oxopregn-4-ene-21-carboxylic acid |
| 1 | *—COOC$_2$H$_5$ | Ethyl 20-methyl-3-oxopregn-4-ene-21-carboxylate |
| 1 | —CONH$_2$ | 20-Methyl-3-oxopregn-4-ene-21-carboxamide |
| 1 | —CHO | 20-Methyl-3-oxopregn-4-ene-21-carboxaldehyde |
| 1 | —CH$_2$OH | 21-(Hydroxymethyl)-20-methylpregn-4-en-3-one |
| 1 | #—CH$_2$O—C=O, phenyl-CH$_2$ | 21-(1-Oxophenylethoxymethyl)-20-methylpregn-4-en-3-one |
| 2 | —COOH | 3-Oxochol-4-en-24-oic acid |
| 2 | *—COOC$_3$H$_7$ | Propyl 3-oxochol-4-en-24-oate |
| 2 | **—CON(C$_2$H$_5$) | N,N-Dimethyl-3-oxochol-4-en-24-amide |
| 2 | —CHO | 3-Oxochol-4-en-20-aldehyde |
| 2 | —CH$_2$OH | 24-Hydroxychol-4-en-3-one |
| 2 | #—CH$_2$OC-phenyl (O double bond) | 24-Benzoyloxychol-4-en-3-one |
| 3 | —COOH | 3-Oxochol-4-ene-24-carboxylic acid |
| 3 | *—COOC$_4$H$_9$ | Butyl-3-oxochol-4-ene-24-carboxylate |
| 3 | **—CON(C$_3$H$_7$)$_2$ | N,N-Dipropyl-3-oxochol-4-ene-24-carboxamide |
| 3 | —CHO | 3-Oxochol-4-ene-24-carboxaldehyde |
| 3 | —CH$_2$OH | 25-Hydroxy-26,27-dinorcholest-4-en-3-one |
| 3 | #—CH$_2$OC—(1-adamantyl) (O double bond) | 25-(1-Adamantylcarbonyloxy)-26,27-dinorcholest-4-en-3-one |
| 4 | —COOH | 3-Oxo-27-norcholest-4-en-26-oic acid |
| 4 | *—COObenzyl | Benzyl-3-oxo-27-norcholest-4-en-26-oate |
| 4 | **—CONH$_2$ | 3-Oxo-27-norcholest-4-en-26-amide |
| 4 | —CHO | 3-Oxo-27-norcholest-4-en-26-aldehyde |
| 4 | —CH$_2$OH | 26-Hydroxy-27-norcholest-4-en-3-one |
| 4 | —CH$_2$OCCH$_3$ (O double bond) | 26-Acetoxy-27-norcholest-4-en-3-one |

*The ester forming group may vary from a straight or branched alkyl group having from 1 to 4 carbon atoms or benzyl, and the nomenclature will vary accordingly.
**The amide forming group may vary from a primary amide wherein R$_3$ and R$_4$ are both hydrogen, to a secondary amide wherein one of R$_3$ or R$_4$ is hydrogen and the other of R$_3$ and R$_4$ is a straight or branched lower alkyl group of from 1 to 4 carbon atoms to a tertiary amide group wherein both R$_3$ and R$_4$ are alkyl of from 1 to 4 carbon atoms, and the nomenclature will vary accordingly.
The nomenclature of other ester forming groups will vary accordingly as the substituent R$_3$ varies.

As set forth hereinabove there is evidence that dihydrotestosterone (DHT) which is a metabolite of testosterone has a stimulatory effect on sebaceous glands and thereby is involved in the pathogenesis of acne, and agents which inhibit the formation of DHT would be useful in the treatment of acne. The compounds employed in the present invention have been found to be inhibitors of testosterone 5α-reductase, the enzyme which transforms testosterone to the more active androgen DHT. Hence, the compounds employed in the present invention, that is, the compounds of general Formulas I to VII, being inhibitors of testosterone 5α-reductase are useful in the treatment of acne and oily skin conditions. Also, compounds employed in the present invention are essentially devoid of any significant systemic endocrine activity.

The utility of the compounds employed in the present invention can be demonstrated by the ability of the compounds to inhibit the activity of human skin testosterone 5α-reductase isolated from human infant foreskin. For example, using skin microsomes containing testosterone 5α-reductase in an amount equivalent to 300 mg of fresh human infant foreskin, and 4-$^{14}$C-testosterone at a concentration of 1.1 × 10$^{-6}$M, 3-oxopregn-4-ene-20-carboxylic acid at 2 × 10$^{-6}$M was found to inhibit the conversion of testosterone to DHT and androstanediol (ADIOL) overall by 88.4%. Using the skin microsomes equivalent to 100 mg of fresh tissue and 4-$^{14}$C-testosterone at a concentration of 1.1 × 10$^{-6}$M, 3-oxopregn-4-ene-20-carboxylic acid at a concentration of 1 × 10$^{-6}$M resulted in an overall 80.9% inhibition of the conversion of testosterone to DHT and ADIOL.

The compounds employed in the present invention are also effective inhibitors of testosterone 5α-reductase in the rat preputial gland and also are effective in reducing the size or activity of the hamster flank organ further demonstrating their activity as inhibitors of the enzyme testosterone 5α-reductase and effectiveness on a sebaceous structure. The lack of systemic or intrinsic endocrinological effects of compounds of general Formulas I to VII can be demonstrated by the lack of binding affinity of the compounds with the androgen receptor of androgen target tissue or by administration of the compounds to laboratory animals, for example, male rats and measuring the effect on secondary sex organs, for example, the seminal vesicles and the ventral prostate. In such test systems it was found that compounds employed in the present invention, for example, 3-oxopregn-4-ene-20-carboxylic acid did not bind rat ventral prostate cytosol androgen receptor at molar concentrations ranging from 10$^{-10}$ to 10$^{-6}$ and at 30 mg/kg/day for 10 days had no stimulatory effect on secondary sex organs of male rats demonstrating a lack of any substantial systemic endocrine effects.

In view of the effectiveness of compounds of Formulas I to VII in reducing or inhibiting the growth of a sebaceous structure said compounds can be said to be, in addition to inhibitors of testosterone 5α-reductase, antiacne agents, anti-serborrheic agents.

To achieve the desired anti-acne or anti-seborrheic effect the compounds employed in the present invention can be administered orally, parenterally, for example, intramuscularly and subcutaneously, and topically to a patient in need of treatment. Topical administration is preferred. As used herein the term patient is taken to mean a warm-blooded mammal, for example, primates, human males and females having an acne condition or an oily skin condition in need of treatment. The compounds of general Formulas I to VII can be administered alone or suitably admixed in the form of a pharmaceutical preparation to the patient being treated. The amount of compound administered will vary with the severity of the acne condition or oily skin condition and repetitive treatment may be desired. For oral and parenteral administration the amount of compound administered, that is, the anti-acne or anti-seborrheic effective amount, is from 0.1 to 50 mg/kg and preferably from 1 to 30 mg/kg. Unit dosages for oral or parenteral administration may contain, for example, from 5 to 200 mg of the active ingredient. For topical administration the anti-acne or anti-seborrheic effective amount of the compounds of general Formulas I to VII on a percent basis can vary from 0.001% to 5% and preferably from 0.005% to 1%. For topical administration the formulated active ingredient, that is, a compound of general Formulas I to VII can be applied directly to the site requiring treatment or can be applied to the oral or nasal mucosa. Applicator sticks carrying the formulation may be employed in administering the compounds. The topical formulation can be, for example, in the form of a solution, suspension, emulsion, gel or cream of either the oil-in-water or water-in-oil type, ointment, paste, jelly, paint or powder. Suitable bases for the topical preparation may be of any conventional type such as oleaginous bases, for example, olive oil, cottonseed oil, petrolatum, white petrolatum, mineral oils, silicones, such as, dimethylpolysiloxane, or methylphenylpolysiloxane, lanolins, polyethyleneglycol, glyceryl monostearate, methylcellulose and hydroxymethylcellulose. The topical formulation may contain pharmaceutically acceptable surfactants, wetting agents, dispersing agents, emulsifiers, penetrants, emollients, detergents, hardeners, preservatives, fillers, antioxidants, perfumes, cooling agents, such as, menthol, soothing agents, such as, camphor, or coloring agents, such as, zinc oxide. Aerosol preparations of a solution, suspension or emulsion containing the active ingredient in the form of a finely ground powder can also be employed for topical administration. The aerosol may be packaged in a pressurized aerosol container together with a gaseous or liquified propellant, for example, dichlorodifluoromethane, dichlorodifluoromethane with dichlorodifluoroethane, carbon dioxide, nitrogen, or propane with the usual adjuvant such as cosolvent and wetting agents as may be necessary or desirable. The compounds may also be administered in a nonpressurized form such as in a nebulizer or atomizer.

Following are illustrative topical pharmaceutical formulations which may be employed in practicing the present invention:

| Solution | |
|---|---|
| 3-Oxopregn-4-ene-20-carboxylic acid | 0.85 g |
| Alcohol | 78.9 ml |
| Isopropyl Myristate | 5.0 g |
| Polyethylene Glycol 400 | 10.0 g |
| Purified Water qs ad | 100 ml |

Combine the alcohol, isopropyl myristate and polyethylene glycol 400 and dissolve the drug substance therein. Add sufficient purified water to give 100 ml.

| A Gel | |
|---|---|
| Methyl-3-oxopregn-4-ene-20-carboxylate | 0.85 g |
| Alcohol | 78.9 ml |
| Isopropyl Myristate | 5.0 g |
| Polyethylene Glycol 400 | 10.0 g |
| Carbopol 940 (Carboxypolymethylene) | 0.75 g |
| Triethylamine | qs |
| Purified Water qs ad | 85 g |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance in the balance of the alcohol and mix well into the batch. Add and mix sufficient purified water to provide 85 g of finished product.

| Applicator Stick | |
|---|---|
| 3-Oxopregn-4-ene-20-carboxylic acid | 0.85 g |
| Absolute Alcohol | 75 ml |
| Polyethylene Glycol 400 | 10.0 g |
| Isopropyl Myristate | 5.0 g |
| Stearic Acid | 4.3 g |
| Sodium Hydroxide | 0.55 g |
| Purified Water qs ad | 85 g |

Combine the absolute alcohol, polyethylene glycol 400 and isopropyl myristate and dissolve the drug substance therein. Add the stearic acid and heat the mixture to about 65° C. Dissolve the sodium hydroxide in a small amount of water, add and mix. Add sufficient water to provide 85 g of finished product. Pour into suitable moulds and allow to solidify.

| Aerosol Foam | |
|---|---|
| 3-Oxopregn-4-ene-20-carboxylic acid | 1.0 g |
| Propylene Glycol | 96.0 g |
| Emulsifying Wax NF XIV | 3.0 g |
| Dichlorodifluoromethane:cryfluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorodifluoromethane:cryfluorane (20:80).

| Topical Cream, Vanishing, o/w | |
|---|---|
| | % w/w |
| 3-Oxopregn-4-ene-20-carboxylic acid | 1 |
| Stearic Acid | 15 |
| Sorbitan Monostearate | 2 |
| Polyoxyethylene Sorbitan Monostearate | 2.3 |
| Propylene Glycol | 5 |
| Methylparaben | 0.025% |
| Propylparaben | 0.015% |
| Purified Water | qs |

| Buccal or Sublingual Tablet | |
|---|---|
| | % w/w |
| 3-Oxopregn-4-ene-20-carboxaldehyde | 1% |
| Calcium Stearate | 1% |
| Calcium Saccharin | 0.02% |
| Granular Mannitol | qs |

Mix and compress on a suitable tablet machine to a weight of 0.115 g/tablet.

| Powder | |
|---|---|
| | % w/w |
| 21-Hydroxy-20-methylpregn-4-en-3-one, micronized | 1 |
| Silicon dioxide, anhydrous | 0.5 |
| Corn starch, lactose, fine powder aa | qs |

| Oleaginous Ointment | |
|---|---|
| | % w/w |
| 3-Oxopregn-4-ene-20-carboxylic acid | 1 |
| White wax | 5 |
| White petrolatum qs | 100 |

| Absorption Ointment Base | |
|---|---|
| | % w/w |
| 20-Methyl-3-oxopregn-4-ene-21-carboxaldehyde | 1 |
| Cholesterol | 3 |
| Stearyl alcohol | 3 |
| White wax | 8 |
| White petrolatum qs | 100 |

| Water Soluble Ointment Base | |
|---|---|
| | % w/w |
| 20-Methyl-3-oxopregn-4-ene-21-carboxylic acid | 1 |
| Polyethylene glycol 4000 | 40 |
| Polyethylene glycol 400 qs | 100 |

| Paste | |
|---|---|
| | % w/w |
| Methyl-3-oxopregn-4-ene-20-carboxylate | 1 |
| Starch | 25 |
| Zinc oxide | 25 |
| White petrolatum qs | 100 |

| Aerosol Foam | |
|---|---|
| | % w/w |
| 3-Oxopregn-4-ene-20-carboxylic acid | 1 |
| Emulsifying wax | 3 |
| Stearic acid | 1 |
| Stearyl alcohol | 1 |
| Diglycol stearate | 2 |
| Propylene glycol | 92 |

For oral administration the compounds can be formulated into solid or liquid preparations, such as, capsules, pills, tablets, troches, powders, solutions, suspensions or emulsions. The compounds can be applied in the form of an aerosol containing finely divided particles of the active ingredient or a solution, suspension, or emulsion of the active ingredient. The solid unit dosage forms can be a capsule which can be of the ordinary gelatin type containing a compound of general Formulas I to VII and a carrier, for example, lubricants and inert filler such as lactose, sucrose, and corn starch. In another embodiment the compounds of general Formulas I to VII can be tableted with conventional tablet bases such as lactose, sucrose, and corn starch in combination with binders such as acacia, corn starch or gelatin, disintegrating agents such as potato starch or aliginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as, propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted succutaneously or intramuscularly as depot injections or implants. Implants may employ inert materials such as biodegradable polymers and synthetic silicones, for example, Silastic, silicone rubber manufactured by the Dow-Corning Corporation.

The following are illustrative pharmaceutical formulations suitable for oral or parenteral administration which may be employed in practicing the present invention:

| Tablet | For 15,000 |
|---|---|
| 3-Oxopregn-4-ene-20-carboxylic acid | 75 g |
| Lactose | 1.216 Kg |
| Corn Starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| | |
|---|---|
| Magnesium Stearate | 0.015 Kg |
| Corn Starch qs ad | 1.725 Kg |

Compress on a suitable tablet machine to a weight of 0.115 g/tablet.

| Soft Gelatin Capsule | |
|---|---|
| 3-Oxopregn-4-ene-20-carboxylic acid | 0.25 Kg |
| Polysorbate 80 | 0.25 Kg |
| Corn Oil qs ad | 25.0 Kg |

Mix and fill into 50,000 soft gelatin capsules.

| IM Depot Injection | |
|---|---|
| Each 1 ml contains the following: | |
| 3-Oxopregn-4-ene-20-carboxylic acid | 5.0 mg |
| Anhydrous Chlorobutanol | 5.0 mg |
| Aluminum Monostearate | 50.0 mg |
| Peanut Oil qs ad | 1.0 ml |

Dissolve or disperse the ingredients in the peanut oil.

| Depot-Implant | |
|---|---|
| 3-Oxopregn-4-ene-20-carboxylic acid | 5 mg |
| Dimethylsiloxane | 240 mg |
| Catalyst qs | |

Disperse the drug substance in the fluid dimethylsiloxane. Add the catalyst and cast into a suitable monolytic structure.

Alternatively, the drug substance may be enclosed by a precast polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate mouldable gel (Hydron).

| IM Injections | |
|---|---|
| A. Oil Type: | |
| 3-Oxopregn-4-ene-20-carboxylic acid | 25 mg |

| -continued | |
|---|---|
| BHA, BHT aa | 0.01% w/v |
| Peanut Oil or Sesame Oil qs | 1.0 ml |
| B. Suspension Type: | |
| 3-Oxopregn-4-ene-20-carboxylic acid | 25 mg |
| Sodium Carboxymethylcellulose | 0.5% w/v |
| Sodium Bisulfite | 0.02% w/v |
| Water for Injection, qs | 1.0 ml |
| Buccal or Sublingual Tablet | |
| 3-Oxopregn-4-ene-20-carboxylic acid | 1% |
| Calcium Stearate | 1% |
| Calcium Saccharin | 0.02% |
| Granular Mannitol | qs |

Mix and compress on a suitable tablet machine to a weight of 0.115 g/tablet.

The compounds of general Formulas I to VII in treating acne and an oily skin condition may be used in combination with other anti-acne preparations, antiseptics, anti-infective agents, keratolytic agents, for example, benzoic acid, resorcinol or salicylic acid, and comedolytic agents, such as, retinoic acid or agents having a retinoic acid-like action, corticoids or other antiinflammatory agents, thioglycolates, ethyl lactate or benzoyl peroxide. The following formulations are illustrative of pharmaceutical preparations for topical application comprising a compound of general Formulas I to VII in combination with a keratolytic agent.

| Aerosol Foam | |
|---|---|
| | % w/w |
| 3-Oxopregn-4-ene-20-carboxylic acid | 1 |
| Resorcinol monoacetate | 1 |
| Emulsifying wax NF | 3 |
| Stearic acid | 1 |
| Stearyl alcohol | 1 |
| Diglycol stearate | 2 |
| Propylene glycol | 91 |

Dissolve the drug substance in the propylene glycol. Add the emulsifying wax and heat to about 70° C. Stir while cooling to room temperature. Charge a suitable aerosol unit with the concentrate and 6.9 g of dichlorodifluoromethane:cryfluorane (20:80).

| A Gel | |
|---|---|
| 3-Oxopregn-4-ene-30-carboxylate | 0.85 g |
| Resorcinol | 0.85 g |
| Alcohol | 78.9 ml |
| Isopropyl myristate | 5.0 g |
| Polyethylene glycol 400 | 10.0 g |
| Carbopol 940 (carboxypolymethylene) | 0.75 g |
| Triethylamine | qs |
| Purified water qs ad | 85 g |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance and the resorcinol in the balance of the alcohol and mix well into the batch. Add and mix sufficient purified water to provide 85 g of finished product.

Many of the compounds employed in the present invention are known and some are commercially available. To applicants' knowledge all of the compounds of general Formulas I to VII are known except compounds of general Formulas II and III wherein $n$ is 4, compounds of Formula IV, compounds of Formulas V and VI wherein $n$ is 1, 3 or 4 and compounds of Formula VI. That is, compounds of the following general Formula VIII are novel compounds:

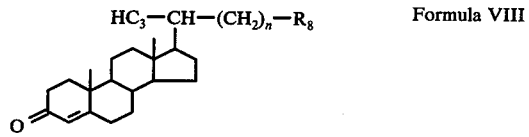

Formula VIII wherein $n$ is 0 to 4, and $R_8$ is COOH, COOR$_9$ wherein R$_9$ is a straight or branched lower alkyl group of from 1 to 4 carbon atoms or benzyl, —CONR$_{10}$R$_{11}$ wherein each of R$_{10}$ and R$_{11}$ is hydrogen or a straight or branched lower alkyl group of from 1 to 4 carbon atoms, CHO, CH$_2$OH, or CH$_2$OR$_{12}$ wherein R$_{12}$ is alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms, with the provisos that when R$_8$ is is COOH or COOR$_9$, $n$ is equal to 4, and when R$_8$ is CHO or CH$_2$OH, $n$ is equal to 1, 3 or 4.

The aldehydes and alcohols employed in the present invention, that is, compounds of Formula I wherein R$_1$ is —CHO or —CH$_2$OR$_5$ and R$_5$ is hydrogen, also represented by the compounds of Formulas V and VI, and the compounds of Formula VII wherein R$_8$ is —CHO or —CH$_2$OH, are obtained from an interrelated sequence of steps starting (A) with the commercially available aldehyde wherein $n$ is 0, that is, 3-oxopregn-4-ene-20-carboxaldehyde, which is reduced to the corresponding alcohol wherein $n$ is 0, that is, 21-hydroxy-20-methylpregn-4-en-3-one using as a reducing agent sodium borohydride or potassium borohydride. This reaction is carried out at temperatures of from about 0° C to about 25° C for from about 1 hour to about 12 hours in a solvent such as a lower alcohol, for example, methanol, isopropyl alcohol or ethanol.

(B) The thus obtained alcohol is converted to the 3-cyclic ethylene acetal, that is, 21-hydroxy-20-methylpregn-4-en-3-one 3-cyclic ethylene acetal using ethylene-glycol and a catalytic amount of a strong acid, for example, p-toluene sulfonic acid or sulfuric acid in a solvent such as benzene, toluene or xylene. This reaction is carried out at the reflux temperature of the solvent for from about 6 hours to about 24 hours. Other acetals at the 3 position may be formed, for example, the 3-cyclic propylene acetal may be formed by substituting for ethylene glycol an appropriate amount of propylene glycol. The acetal derivative is then converted to the corresponding sulfonate, for example, the p-toluene sulfonate, the p-bromophenyl sulfonate or the methane sulfonate derivatives by treatment respectively with p-toluene sulfonylchloride, p-bromophenylsulfonylchloride, or methane sulfonylchloride in a base such as pyridine or a trialkylamine, for example, triethylamine, for from about 2 hours to about 24 hours at a temperature of from about 25° C to about 90° C, and (C) subsequently reacted with methyl methylthiomethylsulfoxide

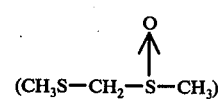

in the presence of a base, such as, sodium hydride or potassium hydride in a solvent such as an ether, for example, tetrahydrofuran or dioxane, or an aromatic hydrocarbon solvent, for example, benzene or toluene for from about 15 minutes to about 4 hours at room temperature to give the next higher chain aldehyde, that is, the aldehyde wherein n is 1, or 20-methyl-3-oxo-pregn-4-ene-21-carboxaldehyde.

20-Methyl-3-oxopregn-4-ene-21-carboxaldehyde is then converted to a corresponding alcohol, that is, 21-(hydroxymethyl)-20-methylpregn-4-en-3-one by the above procedure (A) and the thus obtained alcohol is converted to the 3-cyclic acetal and the 21-sulfonate by the above procedure (B) and subsequently reacted with methyl methylthiomethylsulfoxide by the above procedure (C) to give the next higher chain aldehyde, that is, the aldehyde wherein n is 2, or 3-oxochol-4-en-20-aldehyde. This series of reaction steps is repeated using the end product of procedure (C) as the starting material in procedure (A) until all the aldehydes and alcohols are obtained.

The acid derivatives of the compounds employed in this invention, that is, compounds of Formula I wherein $R_1$ is $COOR_2$, and $R_2$ is hydrogen, also represented by the compounds of Formula II and the compounds of Formula VIII wherein $R_8$ is COOH, are prepared by oxidizing the corresponding aldehydes. The aldehydes are dissolved in a solvent such as acetone, butanone or methylene chloride cooled in an ice bath to 0° to 10° C and treated with sufficient Jones reagent to effect the oxidation. Jones reagent is prepared by standard procedures using 26.72 g of chromium trioxide, 23 ml of concentrated sulfuric acid and water to make 100 ml. The Jones reagent can be added to the solution until the reddish brown color persists.

The esters of the alcohol derivatives employed in the present invention, that is, compounds of general Formula I wherein $R_1$ is —$CH_2OR_5$ and $R_5$ is alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms, also represented by the compounds of general Formula VII, and the compounds of Formula VIII wherein $R_8$ is —$CH_2OR_{12}$, are prepared by reacting the corresponding alcohol derivatives with an appropriate acid anhydride of the formula

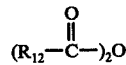

or an acid halide of the formula

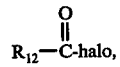

wherein halo is chlorine or bromine and $R_{12}$ is an alkyl group of from 1 to 20 carbon atoms and is straight or branched, a cycloalkyl group of from 5 to 10 carbon atoms, phenyl or phenylalkyl wherein the alkyl moiety has from 1 to 6 carbon atoms and is straight or branched in the presence of a tertiary amine base such as pyridine, quinoline or trialkylamine, which base serves as the solvent, for from 1 to 24 hours at a temperature of from about 25° C to about 100° C. The appropriate acid anhydride or acid halide are known in the art or can be prepared from the corresponding acids by procedures well known in the art.

The ester derivatives of the acids employed in the present invention, that is, compounds of Formula I wherein $R_2$ is other than hydrogen, also represented as compounds of Formula III, and the compounds of Formula VIII wherein $R_8$ is $COOR_9$, are prepared from the corresponding acids. One equivalent of the acid is dissolved in an aprotic solvent, for example, hexamethylphosphorus triamide, dimethyl formamide, or dimethyl sulfoxide and 2 equivalents of a base, such as, sodium hydroxide, potassium hydroxide or potassium carbonate as a 25% solution is added. The reaction mixture is stirred for from 15 minutes to one hour at room temperature afterwhich benzyl halide or an alkyl halide wherein the alkyl moiety has from 1 to 4 carbon atoms and is straight or branched and the halogen is chlorine, fluorine, bromine or iodine is added and stirring is continued for an additional 30 minutes to 4 hours. The product is isolated by conventional means.

The amides employed in the present invention, that is, compounds of Formula I wherein $R_1$ is —$CONR_3R_4$ also represented by the compounds of Formula IV and the compounds of Formula VIII wherein $R_8$ is —$CONR_{10}R_{11}$ are prepared from the corresponding acids by treating one equivalent of the acid with one equivalent of a tertiary amine, such as, a trialkylamine, for example, triethylamine, or pyridine in an ether solvent, such as dioxane or tetrahydrofuran cooled to from $-5°$ to $-25°$ C followed by adding one equivalent of a mixed anhydride, such as, sec-butyl chlorocarbonate, ethyl chlorocarbonate or pivaloyl chloride. The mixture is stirred for from 1/2 hour to 2 hours at a temperature of from $-5°$ to $-25°$ C afterwhich a solution of 2 equivalents of a primary or secondary alkyl amine of the formula —$NR_{10}R_{11}$ or —$NR_3NR_4$ wherein $R_3$, $R_4$, $R_{10}$ and $R_{11}$ have the meanings defined herein except both are not hydrogen in 25 ml of an ether solvent, such as, dioxane or tetrahydrofuran is slowly added with stirring or ammonia is bubbled into the reaction mixture. The reaction mixture is stirred for about one hour at from $-5°$ to $-25°$ C and for about 2 hours at about 25° C then poured into water and the product collected.

The following examples are representative of compounds employed in the present invention.

EXAMPLE 1

21-Hydroxy-20-methylpregn-4-en-3-one

To a solution of 164 g (0.5 m) of 3-oxopregn-4-ene-20β-carboxaldehyde in 2 liters of methanol is added 5.7 g (0.15 m) of sodium borohydride. The reaction is stirred at room temperature for 4 hours, poured into water and made acidic with 10% hydrochloric acid. The methanol is removed under reduced pressure and the organic residue is collected, dried and dissolved in chloroform then treated with 250 g of manganese dioxide and stirred overnight. The inorganic material is removed by filtration and the solvent evaporated to give 21-hydroxy-20-methylpregn-4-en-3-one.

EXAMPLE 2

21-Hydroxy-20-methylpregn-4-en-3-one 3-cyclic ethylene acetal

A mixture of 132 g (0.4 m) of 21-hydroxy-20-methylpregn-4-en-3-one, 200 ml of ethylene glycol and 1 g of p-toluene sulfonic acid in 3 liters of benzene is refluxed overnight. The water is collected in a Dean-Stark trap. The reaction mixture is cooled, treated with a solid sodium bicarbonate and washed with water. The organic layer is dried over potassium carbonate, filtered and the solvent removed yielding 21-hydroxy-20-methylpregn-4-en-3-one 3-cyclic ethylene acetal.

EXAMPLE 3

21-Hydroxy-20-methylpregn-4-en-3-one 3-cyclic ethylene acetal 22-p-toluene sulfonate A mixture of 111 g (0.3 m) of 21-hydroxy-20-methylpregn-4-en-3-one 3-cyclic ethylene acetal and 95 g of p-toluene sulfonyl chloride in 1 liter of pyridine is stirred overnight. The reaction mixture is then poured into ice water and the product collected yielding 21-hydroxy-20-methylpregn-4-en-3-one 3-cyclic ethylene acetal 22-p-toluene sulfonate.

EXAMPLE 4

20-Methyl-3-oxopregn-4-ene-21-carboxaldehyde

To a suspension of 4 g (0.25 m) of sodium hydride in 200 ml of tetrahydrofuran, 25 g (0.2 m) of methyl methylthiomethylsulfoxide is slowly added. The suspension is stirred for one hour followed by the slow addition of 104 g (0.2 m) of 21-hydroxy-20-methylpregn-4-en-3-one 3-cyclic ethylene acetal 22-p-toluene sulfonate in 500 ml of tetrahydrofuran. The reaction mixture is stirred overnight after which the solvent is removed under reduced pressure at 35° C. The residue is taken up in methylene chloride and washed with water. The organic layer is dried over potassium carbonate, filtered and the solvent removed. The remaining solid material is taken up in tetrahydrofuran, treated with 10 ml of 5% hydrochloric acid and after 2 hours water is added and the product isolated to give 20-methyl-3-oxopregn-4-ene-21-carboxaldehyde.

When in the procedure of Example 1 3-oxopregn-4-ene-20$\beta$-carboxaldehyde is replaced by an appropriate amount of 20-methyl-3-oxopregn-4-ene-21-carboxaldehyde, 3-oxochol-4-en-20-aldehyde, 3-oxochol-4-ene-24-carboxaldehyde, or 3-oxo-27-norcholest-4-en-26-aldehyde, the following respective compounds are obtained: 21-(hydroxymethyl)-20-methylpregn-4-en-3-one, 24-hydroxychol-4-en-3-one, 25-hydroxy-26,27-dinorcholest-4-en-3-one, and 26-hydroxy-27-norcholest-4-en-3-one.

When in the procedure of Example 2 21-hydroxy-20-methylpregn-4-en-3-one is replaced with an appropriate amount of 21-(hydroxymethyl)-20-methylpregn-4-en-3-one, 24-hydroxychol-4-en-3-one, 25-hydroxy-26,27-dinorcholest-4-en-3-one, or 26-hydroxy-27-norcholest-4-en-3-one the corresponding 3-cyclic ethylene acetal derivatives are obtained.

When in the procedure of Example 3 an appropriate amount of each of the thus obtained 3-cyclic ethylene acetals is substituted for 21-hydroxy-20-methylpregn-4-en-3-one 3-cyclic ethylene acetal the corresponding p-toluene sulfonate derivatives are obtained.

When in the procedure of Example 4 21-hydroxy-20-methylpregn-4-en-3-one 3-cyclic ethylene acetal 22-p-toluene sulfonate is replaced by an appropriate amount of 21-(hydroxymethyl)-20-methylpregn-4-en-3-one 3-cyclic ethylene acetal 21-p-toluene sulfonate, 24-hydroxychol-4-en-3-one 3-cyclic ethylene acetal 24-p-toluene sulfonate, or 25-hydroxy-26,27-dinorcholest-4-en-3-one 3-cyclic ethylene acetal 25-p-toluene sulfonate the following respective compounds are obtained: 3-oxochol-4-en-20-aldehyde, 3-oxochol-4-ene-24-carboxaldehyde, and 3-oxo-27-norcholest-4-en-26-aldehyde.

EXAMPLE 5

3-Oxopregn-4-ene-20-carboxylic acid

A solution of 34.2 g (0.1 m) of 3-oxopregn-4-ene-20$\beta$-carboxaldehyde in acetone is cooled in an ice bath and 29 ml of Jones reagent slowly added. After the Jones reagent is added the reaction is stirred for 30 minutes then poured into water with stirring. The product is collected yielding 3-oxopregn-4-ene-20-carboxylic acid.

When in the procedure of Example 5 3-oxopregn-4-ene-20$\beta$-carboxaldehyde is replaced with an appropriate amount of 20-methyl-3-oxopregn-4-ene-21-carboxaldehyde, 3-oxochol-4-en-20-aldehyde, 3-oxochol-4-ene-24-carboxaldehyde or 3-oxo-27-norcholest-4-en-26-aldehyde the following respective compounds are obtained: 20-methyl-3-oxopregn-4-ene-21-carboxylic acid, 3-oxochol-4-en-24-oic acid, 3-oxochol-4-ene-24-carboxylic acid and 3-oxo-27-norcholest-4-en-26-oic acid.

EXAMPLE 6

21-(1-Oxoethoxy)-20-methylpregn-4-en-3-one

A mixture of 10 g of 21-hydroxy-20-methylpregn-4-en-20-one, 10 ml of acetic anhydride and 100 ml of pyridine is stirred overnight at room temperature after which the reaction mixture is poured into ice water and stirred for one hour. The product is collected yielding 21-(1-oxoethoxy)-20-methylpregn-4-en-3-one.

When in the procedure of Example 6 acetic anhydride is replaced with an appropriate amount of butyryl chloride, benzoyl chloride, 1-norbornylcarbonyl chloride, or phenylacetic anhydride the following respective products are obtained: 21-(1-oxobutoxy)-20-methylpregn-4-en-3-one, 21-(1-oxobenzyloxy)-20-methylpregn-4-en-3-one, 21-(1-oxo-2-phenylethoxy)-20-methylpregn-4-en-3-one, and 21-(1-oxo-1-norbornylmethoxy)-20-methylpregn-4-en-3-one.

EXAMPLE 7

Methyl 3-oxopregn-4-ene-20-carboxylate

To a solution of 20 g (0.06 m) of 3-oxopregn-4-ene-20-carboxylic acid in 100 ml of hexamethyl phosphorus triamide is added 5.0 g (0.12 m) of sodium hydroxide as a 25% solution. The solution is stirred for 30 minutes after which 34 g (0.24 m) of methyliodide is added and stirring is continued for an additional 30 minutes. The reaction mixture is poured into 500 ml of water, and the product is collected and recrystallized from acetone to yield methyl 3-oxopregn-4-ene-20-carboxylate, M.P. 175°–177° C.

EXAMPLE 8

N,N-Diethyl-3-oxopregn-4-ene-20-carboxamide

A solution of 3.3 g (0.01 m) of 3-oxopregn-4-ene-20-carboxylic acid in 50 ml of tetrahydrofuran is cooled to −10° C and treated with 1.1 g (0.01 m) of triethylamine and 1.36 g (0.01 m) of sec-butyl chlorocarbonate. The solution is stirred for 45 minutes at −10° C after which a solution of 2 g of diethylamine in 25 ml of tetrahydrofuran is added slowly. The reaction mixture is stirred for 1 hour at −10° C and for 2 hours at 25° C and is then poured into water and the product collected.

I claim:

1. A method of treating acne and oily skin in a patient in need thereof which comprises administering to said patient an effective amount of a compound of the formula:

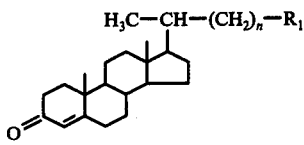

wherein $n$ is an integer of from 0 to 4; $R_1$ is —COOR$_2$, —CONR$_3$R$_4$, —CHO or —CH$_2$OR$_5$; $R_2$ is hydrogen, a straight or branched lower alkyl group of from 1 to 4 carbon atoms, or benzyl; each of $R_3$ and $R_4$ is hydrogen or a straight or branched lower alkyl group of from 1 to 4 carbon atoms; and $R_5$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched, or cycloalkylcarbonyl wherein the cycloalkyl moiety has from 5 to 10 carbon atoms.

2. A method of treating acne in a patient in need thereof which comprises administering to said patient an anti-acne effective amount of a compound of the formula:

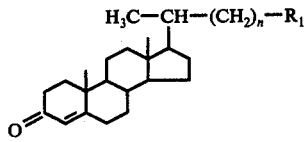

wherein $n$ is an integer of from 0 to 4; $R_1$ is —COOR$_2$, —CONR$_3$R$_4$, —CHO or —CH$_2$OR$_5$; $R_2$ is hydrogen, a straight or branched lower alkyl group of from 1 to 4 carbon atoms, or benzyl; each of $R_3$ and $R_4$ is hydrogen or a straight or branched lower alkyl group of from 1 to 4 carbon atoms; and $R_5$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms.

3. The method of claim 2 wherein the compound is administered as a topical preparation containing from 0.001% to 5% of the compound.

4. The method of claim 2 wherein the compound is administered as a topical preparation containing from 0.005% to 1% of the compound.

5. The method of claim 2 wherein $R_1$ is —COOR$_2$.

6. The method of claim 5 wherein $n$ is the integer 0.

7. The method of claim 6 wherein $R_2$ is hydrogen.

8. The method of claim 6 wherein $R_2$ is methyl.

9. The method of claim 2 wherein $R_1$ is —CH$_2$OR$_5$, and $R_5$ is hydrogen.

10. The method of claim 2 wherein $R_1$ is —CHO.

11. An anti-acne and anti-seborrheic pharmaceutical composition in the form of an ointment, cream or, paste, for topical administration comprising an anti-acne effective amount of a compound of the formula:

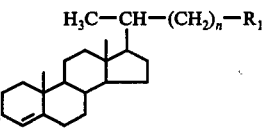

wherein $n$ is an integer of from 0 to 4; $R_1$ is —COOR$_2$, —CONR$_3$R$_4$, —CHO or —CH$_2$OR$_5$; $R_2$ is hydrogen, a straight or branched lower alkyl group of from 1 to 4 carbon atoms, or benzyl; each of $R_3$ and $R_4$ is hydrogen or a straight or branched lower alkyl group of from 1 to 4 carbon atoms; and $R_5$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched, or cycloalkylcarbonyl wherein the cycloalkyl moiety has from 5 to 10 carbon atoms.

12. A process for preparing a compound of the formula:

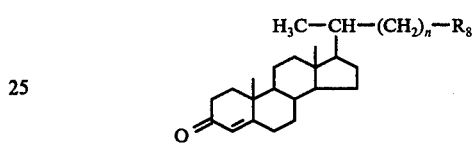

wherein $n$ is an integer of from 0 to 4 and $R_8$ is —CONR$_{10}$R$_{11}$ or —CH$_2$OR$_{12}$ wherein each of $R_{10}$ and $R_{11}$ is hydrogen or a straight or branched lower alkyl group of from 1 to 4 carbon atoms, and $R_{12}$ is alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms which comprises the steps of when $R_8$ is —CONR$_{10}$R$_{11}$ treating one equivalent of the corresponding acid with one equivalent of a tertiary amine in an ether solvent cooled to $-5°$ to $-25°$ C, adding one equivalent of a mixed anhydride selected from sec-butyl chlorocarbonate or ethyl chlorocarbonate and pivaloyl chloride, stirring the mixture for from ½ hour to 2 hours at a temperature of from $-5°$ to $-25°$ C slowly adding with stirring a solution of 2 equivalents of a primary or secondary alkyl amine of the formula —NR$_{10}$R$_{11}$ wherein $R_{10}$ and $R_{11}$ have the meanings defined in claim 1 except both are not hydrogen in an ether, or bubbling ammonia into the reaction mixture and stirring for 1 hour at from $-5°$ to $-25°$ C and for 2 hours at about 25° C afterwhich the reaction mixture is poured into water and the product collected and when $R_8$ is —CH$_2$OR$_{12}$ reacting the corresponding alcohol with an acid anhydride of the formula

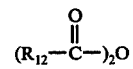

or an acid halide of the formula

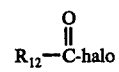

wherein $R_{12}$ has the meaning defined above and halo is chlorine or bromine in the presence of a tertiary amine base for from 1 to 24 hours at a temperature of from about 25° C to 100° C.

* * * * *